US006245923B1

(12) United States Patent
Sulzbach et al.

(10) Patent No.: US 6,245,923 B1
(45) Date of Patent: Jun. 12, 2001

(54) RECOVERY OF HIGHLY FLUORINATED CARBOXYLIC ACIDS FROM THE GASEOUS PHASE

(75) Inventors: Reinhard Albert Sulzbach, Burghausen; Rainer Grasberger, Garching, both of (DE); Rik A. Brandenburg, Gorinchem (NL)

(73) Assignees: Dyneon GmbH (DE); E. I. DuPont de Nemours & Co., Wilmington, DE (US)

( * ) Notice: Subject to any disclaimer, the term of this patent is extended or adjusted under 35 U.S.C. 154(b) by 0 days.

(21) Appl. No.: 09/214,456

(22) PCT Filed: Jul. 30, 1997

(86) PCT No.: PCT/EP97/04146

§ 371 Date: Jan. 5, 1999

§ 102(e) Date: Jan. 5, 1999

(87) PCT Pub. No.: WO98/05621

PCT Pub. Date: Feb. 12, 1998

(30) Foreign Application Priority Data

Aug. 5, 1996 (DE) .............................................. 196 31 406

(51) Int. Cl.$^7$ ...................................................... C11B 13/00
(52) U.S. Cl. ........................... 554/195; 562/605; 423/179
(58) Field of Search ............................ 554/195; 562/605; 423/179

(56) References Cited

U.S. PATENT DOCUMENTS 4,060,535   11/1977   Cinco ................................... 260/414

FOREIGN PATENT DOCUMENTS

| 24 32 473 | 7/1974 | (DE) | ............................... C07C/53/00 |
| 195 27 276 | 7/1995 | (DE) | ............................... C07C/53/21 |

*Primary Examiner*—Deborah D. Carr
(74) *Attorney, Agent, or Firm*—James V. Lilly

(57) ABSTRACT

The process for the recovery of highly fluorinated carboxylic acids from off-gas streams, in which the off-gas is brought into contact with an alkaline washing solution of density >1.15 g/cm$^3$ so that the salt of the highly fluorinated carboxylic acid settles out as a separate phase, proceeds particularly advantageously when the alkaline washing solution is a potassium carbonate solution.

1 Claim, No Drawings

RECOVERY OF HIGHLY FLUORINATED CARBOXYLIC ACIDS FROM THE GASEOUS PHASE

This application is a 371 of PCT/EP97/04146 filed Jul. 30, 1997.

DESCRIPTION

German Patent 195 27 276 (Patent Specification published on Aug. 08, 1996) relates to a process for the recovery of highly fluorinated carboxylic acids from off-gas streams, wherein the off-gas is brought into contact with an alkaline washing solution of density >1.15 g/cm$^3$ so that the salt of the highly fluorinated carboxylic acid settles out as a separate phase.

As a further development of this inventive conception, it has now been found that the alkaline washing solution used is advantageously a potassium carbonate solution. The invention thus relates to a process for the recovery of highly fluorinated carboxylic acids from off-gas streams, in which the off-gas is brought into contact with an alkaline washing solution of density >1.15 g/cm$^3$ so that the salt of the highly fluorinated carboxylic acid settles out as a separate phase, wherein the alkaline washing solution used is a potassium carbonate solution.

When the alkaline washing solution in the process of German Patent 195 27 276 is an alkali metal hydroxide solution, the corresponding carbonate is formed if the off-gas stream to be purified contains carbon dioxide. It has now been found that, when using sodium hydroxide solution, this sodium carbonate leads to encrustation in the scrubbing column. This formation of carbonate is furthermore associated with an undesirable consumption of sodium hydroxide. The use of potassium carbonate as the alkaline agent avoids these disadvantages.

If sodium carbonate is used instead of potassium carbonate, no sodium hydroxide is consumed but there is a considerable increase in encrustation. Moreover, sodium carbonate has a less favorable solubility behavior. This is shown by the fact that the cooling of sodium carbonate solutions of the density required for the process results in precipitation due to super-saturation. This is not the case with potassium carbonate, so it is not necessary to heat pipelines and vessels.

It has further been found that when potassium carbonate is used as the alkaline agent, the potassium salt of the highly fluorinated carboxylic acid is deposited in a form which is easier to filter off than when potassium hydroxide solution is used. This is coupled with the abovementioned advantage that when potassium carbonate is used, there is no consumption of alkaline agent by absorbed carbon dioxide.

The density of the alkaline washing solution is advantageously 1.2 to 1.4 g/cm$^3$.

Reference is made to the main patent for further details.

The invention will now be illustrated further by means of the following example.

EXAMPLE

400 Nm$^3$/h of off-gas from a process for drying powdered fluorinated polymer, at a temperature of 171° C., are introduced into a commercially available scrubbing column of length 2000 mm and internal diameter 250 mm. The off-gas contains 750 mg/Nm$^3$ of perfluorooctanoic acid, corresponding to 300 g/h. Circa 20 kg/h of water are additionally conveyed with the off-gas from the dryer into the scrubbing process. The pressure in the scrubbing column is circa 1 bar absolute.

10 m$^3$/h of an alkaline washing liquor, consisting essentially of aqueous potassium carbonate solution of density 1.30 g/cm$^3$, at a temperature of 45° C., are introduced into the scrubber via a nozzle. The purified off-gas stream of 400 Nm$^3$/h, now containing only 0.8 mg/Nm$^3$ of perfluorooctanoic acid, corresponding to 0.32 g/h, escapes from the lower section of the scrubbing column. Water vapor, corresponding to the water partial pressure, is additionally present at the temperature of circa 45° C. prevailing in the scrubber.

The scrubber is operated in co-current. The alkaline washing medium and the potassium salt of perfluorooctanoic acid which is formed flow out of the column directly into a separating vessel of volume 0.4 m$^3$, where the potassium salt of perfluorooctanoic acid, which is insoluble in the alkaline washing solution, floats to the top as a pulpy layer. The alkaline washing solution, which now contains practically no potassium salt of perfluorooctanoic acid, is withdrawn from the bottom of the separating vessel and pumped back into the scrubbing column. The concentration of dissolved potassium salt of perfluorooctanoic acid in the washing medium is about 170 mg/l. The density of the washing liquor is maintained at the desired value of about 1.30 g/cm$^3$ by the addition of potassium carbonate. The potassium salt of perfluorooctanoic acid which has separated out as a pulpy layer runs off into a tank through an overflow on the separating vessel, together with some washing medium. The discharge process is aided by a very slow stirrer immersed directly in the upper layer. In the separating vessel, the separation of the washing solution and the potassium perfluorooctanoate foam formed is very good.

After standing for several hours, a further two phases separate out in the tank: a lower phase consisting essentially of excess washing liquor, and a pulpy upper phase. The lower phase is separated off and recycled into the washing process.

The pulpy upper phase contains 36% by weight of potassium perfluorooctanoate.

The concentrate obtained in this way is subjected to further working-up to give pure 100% by weight perfluorooctanoic acid.

It may be mentioned that although the concentrate obtained in this way is a stirrable and pumpable mixture, it does not constitute a stable solution of the potassium salt of perfluorooctanoic acid. To obtain a stable solution, it would be necessary to add even more water. However, this is not absolutely necessary for further working-up.

Because the lower phase which has been separated off is recycled into the washing process as described, no perfluorooctanoic acid is lost. There is no observable impairment of the washing process due to encrustation in the column after several weeks of operation.

What is claimed is:

1. A process for the recovery of highly fluorinated carboxylic acids from off-gas streams, in which the off-gas is brought into contact with an alkaline washing solution of density >1.15 g/cm$^3$ so that the salt of the highly fluorinated carboxylic acid settles out as a separate phase, wherein the alkaline washing solution used is a potassium carbonate solution.

* * * * *